United States Patent
Ueno et al.

(10) Patent No.: US 7,062,968 B2
(45) Date of Patent: Jun. 20, 2006

(54) TEMPERATURE CONTROL APPARATUS FOR HUMIDITY SENSOR

(75) Inventors: Masaki Ueno, Saitama-ken (JP); Kei Machida, Saitama-ken (JP); Tetsuo Endo, Saitama-ken (JP); Hideharu Yamazaki, Saitama-ken (JP)

(73) Assignee: Honda Giken Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/322,470

(22) Filed: Dec. 19, 2002

(65) Prior Publication Data

US 2003/0115943 A1    Jun. 26, 2003

(30) Foreign Application Priority Data

Dec. 21, 2001 (JP) ............................. 2001-390147

(51) Int. Cl.
*G01N 27/04* (2006.01)
(52) U.S. Cl. ................. 73/335.05; 73/335.03; 73/29.01; 73/25.04
(58) Field of Classification Search ............ 73/335.05, 73/335.03, 29.01, 25.04
See application file for complete search history.

(56) References Cited

U.S. PATENT DOCUMENTS

| 3,599,862 | A | * | 8/1971 | Hogan et al. ............... 236/4 |
| 4,080,564 | A | * | 3/1978 | Nitta et al. ................. 324/703 |
| 4,143,177 | A | * | 3/1979 | Kovac et al. ................ 427/79 |
| 4,203,087 | A | * | 5/1980 | Kovac et al. ................ 338/35 |
| 4,313,338 | A | * | 2/1982 | Abe et al. ................... 73/31.06 |
| 4,801,211 | A | * | 1/1989 | Yagi et al. ................... 374/28 |
| 4,812,615 | A | * | 3/1989 | Manzoni ..................... 219/209 |
| 5,644,080 | A | * | 7/1997 | Stormbom et al. ......... 73/335.05 |
| 5,846,831 | A | * | 12/1998 | Silvis ........................ 436/55 |
| 6,073,480 | A | * | 6/2000 | Gokhfeld ................... 73/29.02 |
| 6,581,370 | B1 | * | 6/2003 | Sato et al. .................. 60/277 |
| 6,641,303 | B1 | * | 11/2003 | Yamazaki et al. .......... 374/144 |
| 2002/0040598 | A1 | * | 4/2002 | Sugaya et al. ............. 73/335.02 |
| 2002/0168772 | A1 | * | 11/2002 | Lloyd et al. ............... 436/37 |

FOREIGN PATENT DOCUMENTS

JP            58009054 A    *   1/1983

* cited by examiner

*Primary Examiner*—Michael Cygan
(74) *Attorney, Agent, or Firm*—Westerman, Hattori, Daniels & Adrian, LLP

(57) ABSTRACT

A temperature control apparatus for a humidity sensor is provided for preventing impurities from sticking on a sensor element, while protecting the sensor element from cracking due to the humidity sensor heated by a heater in the presence of condensation, to maintain a high detection accuracy of the humidity sensor. The temperature control apparatus is configured to control the temperature of a sensor element of a humidity sensor disposed in an exhaust passage of an internal combustion engine for detecting the humidity within the exhaust passage. The temperature control apparatus comprises a heater for heating the sensor element, a temperature sensor for detecting the temperature of the sensor element, and an ECU for controlling a heating amount of the heater to bring the detected temperature of the sensor element to a first predetermined temperature during an operation of the internal combustion engine.

5 Claims, 11 Drawing Sheets

TEMPERATURE CONTROL APPARATUS FOR HUMIDITY SENSOR

BACKGROUND OF THE INVENTION

1. Field of the Invention

The present invention relates to a temperature control apparatus for controlling the temperature of a sensor element of a humidity sensor disposed in an exhaust passage of an internal combustion engine for detecting the humidity within the exhaust passage in order to maintain a good condition for the sensor element.

2. Description of the Prior Art

Some internal combustion engines are provided with an adsorbent in its exhaust system for adsorbing hydrocarbons in exhaust gases upon starting. The adsorbent has, for example, zeolite on the surface such that hydrocarbons in exhaust gases introduce into pores of zeolite when they pass through the adsorbent, and are adsorbed by the adsorbent. The adsorbent desorbs the hydrocarbons once adsorbed thereby when the adsorbent is heated by exhaust gases to a predetermined temperature or higher (for example, 100–250° C.), permitting the desorbed hydrocarbons to be recirculated to the internal combustion engine through an EGR pipe and the like. While the adsorbent repeats the adsorption and desorption of hydrocarbons as described above, the remaining amount of hydrocarbons not desorbed may gradually increase in the adsorbent, or pores of the adsorbent may be broken during a long-term use. As a result, the adsorbent is deteriorated, possibly causing a gradual degradation in the ability of the adsorbent to adsorb the hydrocarbons. It is therefore necessary to determine the state, more particularly, a deterioration of the adsorbent.

The applicant has already proposed a deterioration determining apparatus for determining a deterioration of an adsorbent as described above, for example, in Japanese Patent Application No. 2001-323811. This deterioration determining apparatus relies on a proportional relationship between the abilities of the adsorbent to adsorb hydrocarbons and moisture to determine a degradation in the abilities of the adsorbent to adsorb hydrocarbons and moisture, i.e., a deterioration of the adsorbent by detecting the humidity in exhaust gases using a humidity sensor after they pass the adsorbent. The humidity sensor comprises a sensor element which is made of a porous material having a large number of pores, and detects the humidity of exhaust gases as moisture in the exhaust gases introduces into the pores and is adsorbed therein when it passes through the sensor element. In this way, the humidity is detected with the sensor element exposed to exhaust gases, so that impurities such as water droplets produced by condensation, unburnt fuel components included in the exhaust gases, and the like can stick to the sensor element, in which case the humidity sensor fails to correctly detect the humidity of exhaust gases, resulting in the inability to correctly detect a deterioration of the adsorbent. To solve this problem, the deterioration determining apparatus performs heat cleaning by heating the sensor element using a heater for removing water droplets and the like sticking on the sensor element to recover the detection accuracy of the humidity sensor.

Specifically, in the heat cleaning, the heater is operated for the predetermined time period when the intake temperature is lower than a predetermined temperature before the start of the internal combustion engine, or when an idling operation continues for a predetermined time period or longer after the start of the internal combustion engine, on the assumption that the sensor element experiences condensation.

In the heat cleaning control described above, the heater is operated for a predetermined time period only in a situation in which it is assumed that the sensor element experiences condensation. However, during a normal operation of the internal combustion engine, impurities other than water droplets within exhaust gases may also stick to the sensor element. However, the heat cleaning is not performed when it is not assumed that the sensor element experiences condensation even if such impurities stick on the sensor element, resulting in a degraded accuracy of detection by the humidity sensor. In addition, since the heater is merely operated for a predetermined time period, the heat cleaning control may fail to sufficiently remove impurities or operate the heater for useless depending on, for example, a temperature state of an exhaust system and the like. Moreover, since the sensor element is suddenly heated by the heater in the presence of condensation, a sudden increase in the temperature of the sensor element from a low temperature, resulting from the heating, would possibly cause cracking of the sensor element.

OBJECT AND SUMMARY OF THE INVENTION

The present invention has been made to solve the problem mentioned above, and it is an object of the invention to provide a temperature control apparatus for a humidity sensor which is capable of preventing impurities from sticking on a sensor element, while protecting the sensor element from cracking due to the humidity sensor heated by a heater in the presence of condensation, to maintain a high accuracy of detection by the humidity sensor.

To achieve the above object, the present invention provides a temperature control apparatus for controlling a temperature of a sensor element of a humidity sensor disposed in an exhaust passage of an internal combustion engine for detecting a humidity within the exhaust passage. The temperature control apparatus is characterized by comprising a heater for heating the sensor element; temperature detecting means for detecting the temperature of the sensor element; and heater control means for controlling the heater to converge the detected temperature of the sensor element to a first predetermined temperature during an operation of the internal combustion engine.

According to this temperature control apparatus for a humidity sensor, the sensor element is heated by the heater to bring the actual temperature of the sensor element of the humidity sensor to the first predetermined temperature during an operation of the internal combustion engine. Since the sensor element is thus maintained at a high temperature during the operation of the internal combustion engine, impurities in exhaust gases can be prevented from sticking on the sensor element. It is therefore possible to maintain a high detection accuracy of the humidity sensor.

Preferably, in the temperature control apparatus for a humidity sensor, the heater is configured to vary its heating amount in response to the amount of power supplied thereto, wherein the heater control means controls the amount of power supplied to the heater in a feedback manner to bring the temperature of the sensor element to the first predetermined temperature.

According to this preferred embodiment of the temperature control apparatus for a humidity sensor, since the heater control means controls the amount of power supplied to the heater in a feedback manner to bring the actual temperature of the sensor element to the first predetermined temperature, impurities in exhaust gases can be prevented from sticking on the sensor element, while minimizing the power consumed by the heater. In addition, it is possible to maintain a high detection accuracy of the humidity sensor.

Preferably, in the temperature control apparatus for a humidity sensor, the heater control means controls the heater with a smaller heating amount when the temperature of the sensor element is converged to the first predetermined temperature than when the temperature of the sensor element is lower than a second predetermined temperature lower than the first predetermined temperature.

According to this preferred embodiment of the temperature control apparatus for a humidity sensor, the heater control means controls the heater with a smaller heating amount when the temperature of the sensor element is brought to the first predetermined temperature than when the temperature of the sensor element is lower than a second predetermined temperature. With this meticulous control, the temperature of the sensor element slowly rises at low temperatures at which the sensor may element suffer from condensation, so that the condensation can be eliminated with minimum power consumption while ensuring the prevention of the sensor element from cracking due to a sudden change in temperature.

Preferably, the temperature control apparatus for a humidity sensor further comprises a characteristic change parameter calculating means for calculating a characteristic change parameter indicative of a degree of a change in the characteristic of the humidity sensor based on a result detected by the humidity sensor, wherein the heater control means controls the heater to bring the temperature of the sensor element to a fourth predetermined temperature lower than the second predetermined temperature or lower while the characteristic change parameter calculating means is calculating the characteristic change parameter.

According to this preferred embodiment of the temperature control apparatus for a humidity sensor, the heater control means control the heater to bring the temperature of the sensor element to a fourth predetermined temperature lower than the second predetermined temperature or lower while the characteristic change parameter calculating means is calculating the characteristic change parameter. Thus, the humidity sensor can detect the humidity with the sensor element being controlled at a temperature at which the sensor element exactly presents a change in the characteristic thereof. As such, the characteristic change parameter can be properly calculated based on the detected humidity.

Preferably, in the temperature control apparatus for a humidity sensor, the heater control means controls the heater to bring the temperature of the sensor element to a third predetermined temperature higher than the first predetermined temperature or higher when the calculated characteristic change parameter is larger than a predetermined value.

According to this preferred embodiment of the temperature control apparatus for a humidity sensor, the heater control means controls the heater to converge the temperature of the sensor element to a third temperature higher than the first predetermined temperature or higher when the calculated characteristic change parameter is larger than a predetermined value. Thus, when the humidity sensor presents a large change in the characteristic due to impurities in exhaust gases which stick on the sensor element, the impurities can be removed at the higher third predetermined temperature, thereby making it possible to recover the original characteristic of the humidity sensor and hence the detection accuracy of the humidity sensor.

DETAILED DESCRIPTION OF THE EMBODIMENT

Figure 1:
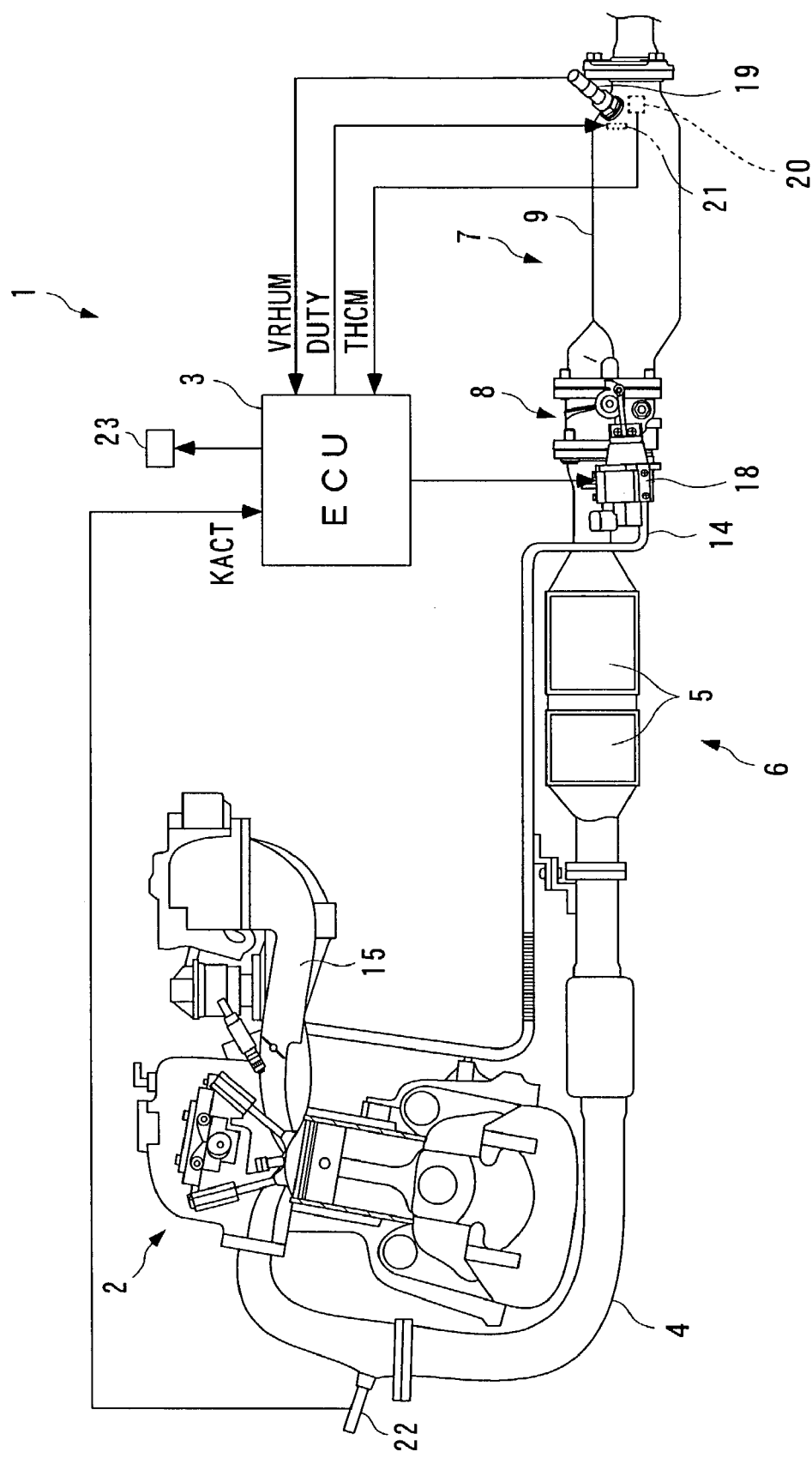
FIG. 1 is a diagram illustrating the configuration of an internal combustion engine which employs a temperature control apparatus for a humidity sensor according to one embodiment of the present invention.

In the following, a preferred embodiment of the present invention will be described in detail with reference to the accompanying drawings. FIG. 1 illustrates an internal combustion engine (hereinafter called the "engine") 2 which employs a temperature control apparatus for a humidity sensor 1 (hereinafter simply called the "control apparatus") according to one embodiment of the present invention. As illustrated in FIG. 1, the control apparatus 1 comprises an ECU 3 (which implements a heater control means and a characteristic change parameter calculating means) which executes control processing, later described.

A catalyzer 6 having two three-way catalysts 5, and a hydrocarbon adsorber 7 for adsorbing hydrocarbons are provided in this order from the upstream side, halfway in an exhaust pipe (exhaust passage) 4 of the engine 2 for purifying exhaust gases. The two three-way catalysts 5 of the catalyzer 6 are arranged adjacent to each other along the exhaust pipe 4, and purify harmful substances (hydrocarbons (HC), carbon monoxide (CO) and nitrogen oxides (NOx)) in exhaust gases passing through the catalyzer 6 by oxidation-reduction catalyst actions, when they are heated to a predetermined temperature (for example, 300° C.) or higher and activated.

Figure 2:
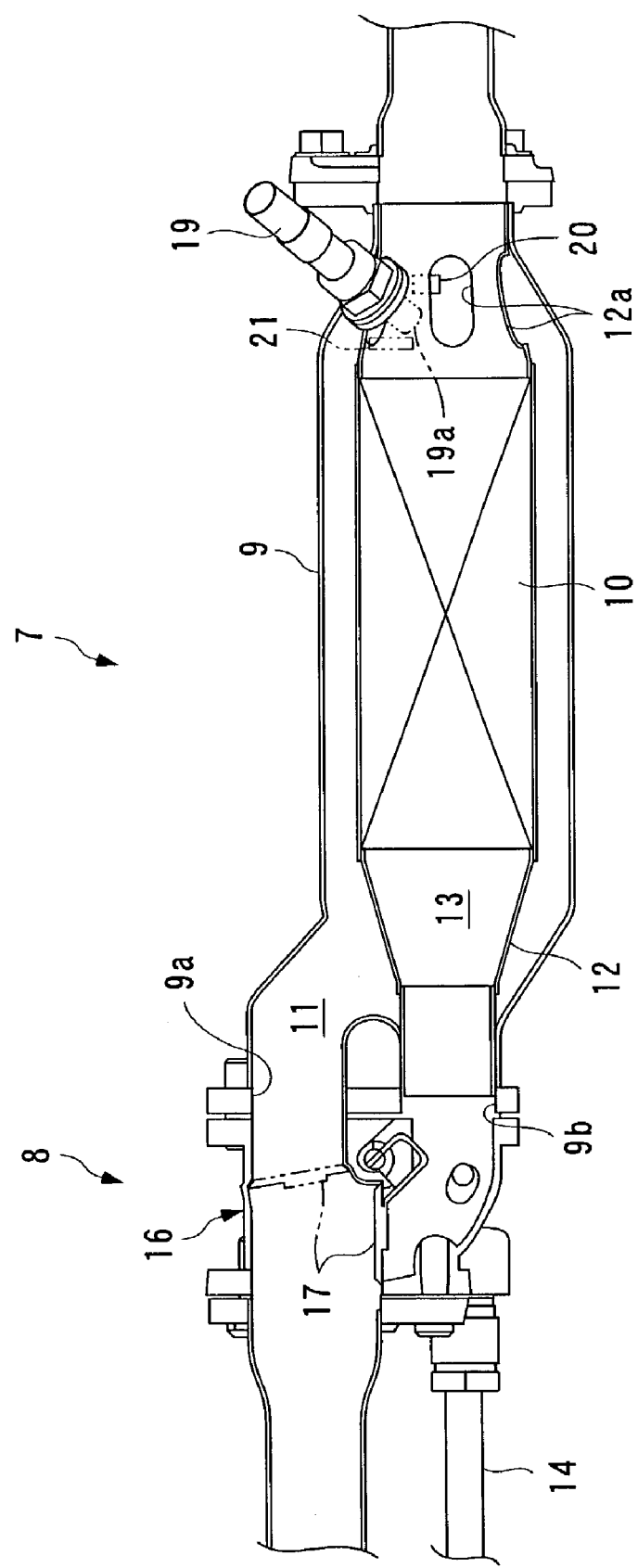
FIG. 2 is an enlarged cross-sectional view illustrating a hydrocarbon adsorber.

The hydrocarbon adsorber 7 in turn is provided for reducing the amount of hydrocarbons emitted to the atmosphere by adsorbing hydrocarbons in exhaust gases during a starting period (for example, for approximately 30 to 40 seconds from the start) of the engine 2 in a state in which the three-way catalysts 5 have not been activated. As illustrated in FIGS. 1 and 2, the hydrocarbon adsorber 7 comprises an exhaust passage switch 8; a substantially cylindrical case 9 defining an outer shell; and a cylindrical adsorbent 10 arranged within the case 9 for adsorbing hydrocarbons in exhaust gases.

As illustrated in FIG. 2, the case 9 has its upstream end divided into two, i.e., an upper and a lower opening 9a, 9b. The upper opening 9a is in communication with a main exhaust passage 11 of the exhaust pipe 3. In addition, a bypass exhaust pipe 12 is connected to inner surfaces of the lower opening 9b and a downstream end of the case 9 in an air tight state. The lower opening 9b is in communication with a bypass exhaust passage 13 which defines an inner space of the bypass exhaust pipe 12. The bypass exhaust pipe 12 is formed with a plurality (for example, five) of elongated communication holes 12a at a predetermined location near the downstream end in the circumferential direction at equal intervals, such that the downstream end of the main exhaust passage 11 is in communication with the downstream end of the bypass exhaust passage 13 through these communication holes 12a 11 within the case 9.

The adsorbent 10 is comprised of a honeycomb core, made of a metal, which carries zeolite on its surface. The zeolite, which has high heat resistant properties, adsorbs hydrocarbons at low temperatures (for example, below 100° C.), and desorbs hydrocarbons once adsorbed thereby at a predetermined temperature or higher (for example, 100–250° C.). Then, the desorbed hydrocarbons are recirculated to the engine 2 from the hydrocarbon adsorber 7 through an EGR pipe 14 and an intake pipe 15, and burnt by the engine 2.

The exhaust passage switch 8 comprises a substantially cylinder coupling pipe 16 for coupling the hydrocarbon adsorber 7 to the catalyzer 6; and a switching valve 17 arranged in the coupling pipe 16 for switching the passage of exhaust gasses between the main passage 11 or bypass passage 13. The switching valve 17 is controlled by a switching valve driving controller 18 (see FIG. 1) which is driven by the ECU 3.

In the exhaust passage switch 8 configured as described above, the switching valve 17 is generally rotated to a position indicated by a two-dot chain line in FIG. 2 immediately after a start of the engine 2 to switch the exhaust passage to the bypass exhaust passage 13. In this way, exhaust gases passing through the catalyzer 6 flow downstream along the bypass exhaust passage 13 and are emitted to the outside after hydrocarbons and moisture contained therein are adsorbed by the adsorbent 10. Subsequently, as the three-way catalysts 5 of the catalyzer 6 are activated after the lapse of a certain time from the start of the engine 2, the switching valve 17 is rotated to a position indicated by a solid line in FIG. 2 to switch the exhaust passage to the main exhaust passage 11. In this way, exhaust gases passing through the catalyzer 6 flow along the main exhaust passage 11 within the case 9, flow into the bypass exhaust pipe 12 through the communication holes 12a in the downstream end portion of the bypass exhaust pipe 12, further flow downstream, and eventually are emitted to the outside.

A humidity sensor 19 is attached at a location downstream of the hydrocarbon adsorber 7 for detecting the humidity of exhaust gases to determine a deterioration of the adsorbent 10. The humidity sensor 19 has a sensor element 19a made of a porous material such as alumina or the like, the resistance value of which changes in accordance with the amount of moisture in exhaust gases adsorbed by the adsorbent 10 to detect the humidity of the exhaust gases. The humidity sensor 19 outputs a value VRHUM indicative of the detected humidity to the ECU 3. Thus, the detected value VRHUM presents a lower value as the humidity is higher.

A label resistive element (not shown) is also incorporated in the humidity sensor 19. The label resistive element has a resistance value LBLR which is selected in accordance with the previously measured output characteristic of each humidity sensor 19. The resistance value LBLR is read by the ECU 3, so that the output characteristic of the humidity sensor 19 can be known. A temperature sensor 20 comprised of a thermistor or the like is disposed near the sensor element 19a for detecting the temperature THCM of the sensor element 19a (hereinafter called the "sensor element temperature"). A detection signal indicative of the temperature THCM is outputted to the ECU 3. A heater 21 is disposed near the humidity sensor 19 for heating the sensor element 19a. The heater 21 generates the amount of heat which is controlled in response to an energization duty ratio DUTY controlled by the ECU 3. While the heater 21 and sensor element 19a are separately shown in FIGS. 1 and 2 for convenience of description, the heater 21 is actually constructed to directly heat the sensor element 19a. Alternatively, the temperature sensor 20 may be integrally formed with the sensor element 19a, such that the sensor element temperature THCM is detected based on a change in the resistance of the sensor element 19a. Further alternatively, the temperature of the sensor element 19a may be estimated through a calculation in accordance with an operating condition of the engine 2, instead of the temperature sensor 20 provided for detecting the temperature of the sensor element 19a.

A proportion type air/fuel ratio sensor (hereinafter called the "LAF sensor") 22 is disposed at a location upstream of the catalyst 6 in the exhaust pipe 4. The LAF sensor 22 linearly detects an oxygen concentration (air/fuel ratio) of exhaust gases to output a detected value KACT to the ECU 3. The detected value KACT is represented by an equivalent value proportional to an inverse of the air/fuel ratio, and is set to 1.0 when the air/fuel ratio is equal to the stoichiometric air/fuel ratio and to a value smaller than 1.0 when the air/fuel ratio is leaner than the stoichiometric air/fuel ratio.

An alarm lamp 23 is also connected to the ECU 3. The ECU 3 turns on the alarm lamp 23 when it determines that the humidity sensor 19 fails in order to let the operator know the failure.

The ECU 3 may be based on a microcomputer which is comprised of an I/O interface, a CPU, a RAM, a ROM, and the like. The respective signals detected by a variety of the aforementioned sensors are inputted to the CPU after subjected to A/D conversion in the I/O interface. The CPU performs a heater control procedure in the following manner for controlling the temperature of the humidity sensor 19 in accordance with a control program and the like stored in the ROM in response to the detection signals from the sensors.

Figure 3:
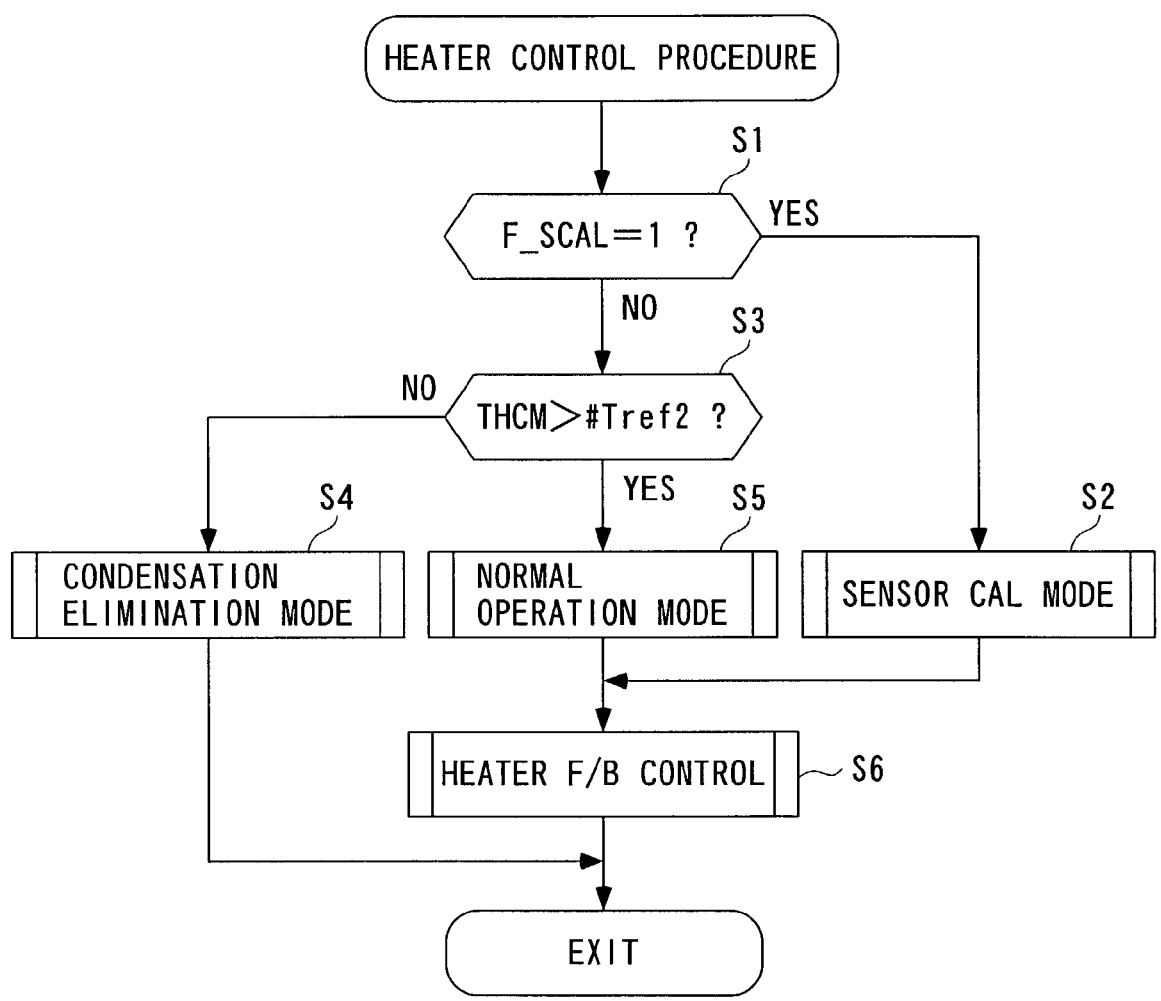
FIG. 3 is a flow chart illustrating a main routine of a heater control procedure.

FIG. 3 is a flow chart illustrating a main routine of the heater control procedure. The routine is executed every predetermined time (for example, 100 ms). First, at step 1 (labeled as "S1" in the figure. The same applies to the subsequent figures), it is determined whether or not an execution condition establishment flag F_SCAL is "1." As described later, the execution condition establishment flag F_SCAL is set to "1" when a condition is established for executing a sensor CAL mode. If the answer to step 1 is YES, showing that the condition is established for executing the sensor CAL mode, the CPU executes the sensor CAL mode as a heater control mode at step 2, followed by the routine proceeding to the next step. The sensor CAL mode involves a calculation of a correction amount COR_TMTRS (characteristic change parameter) indicative of the degree of a change in the characteristic of the humidity sensor 19, details of which will be described later.

If the answer to step 1 is NO, showing that the condition is not established for executing the sensor CAL mode, it is determined whether or not the sensor element temperature THCM detected by the temperature sensor 20 is higher than a second predetermined temperature #Tref2 (for example, 70° C.) (step 3). If the answer to step 3 is NO, the CPU executes a condensation elimination mode at next step 4 on the assumption that the sensor element 19a is in a low temperature condition in which condensation can occur, followed by termination of the heater control main routine.

Figure 4:
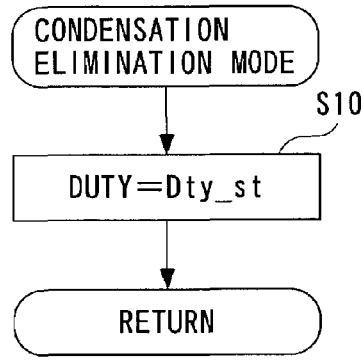
FIG. 4 is a flow chart illustrating a subroutine of a condensation elimination mode at step 4 in FIG. 3.

FIG. 4 illustrates a subroutine of the condensation elimination mode. In this subroutine, the CPU sets the energization duty ratio DUTY for the heater 21 to a predetermined value Dty_st (for example, 40%) (step 10). In this way, the energization duty ratio DUTY is set to a relatively small value to heat the sensor element 19a with a small heating amount when the temperature THCM of the sensor 19a is low to possibly cause condensation.

Turning back to FIG. 3, if the answer to step 3 is YES, showing that THCM>#Tref2, on the other hand, the CPU executes a normal operation mode as the heater control mode on the assumption that the sensor 19a is free from condensation (step 5). Then, at step 6 subsequent to step 2 or 5, the CPU executes a feedback control for the heater 21 (hereinafter called the "heater F/B control"), followed by termination of the heater control main routine. The heater F/B control will be later described.

Figure 5:
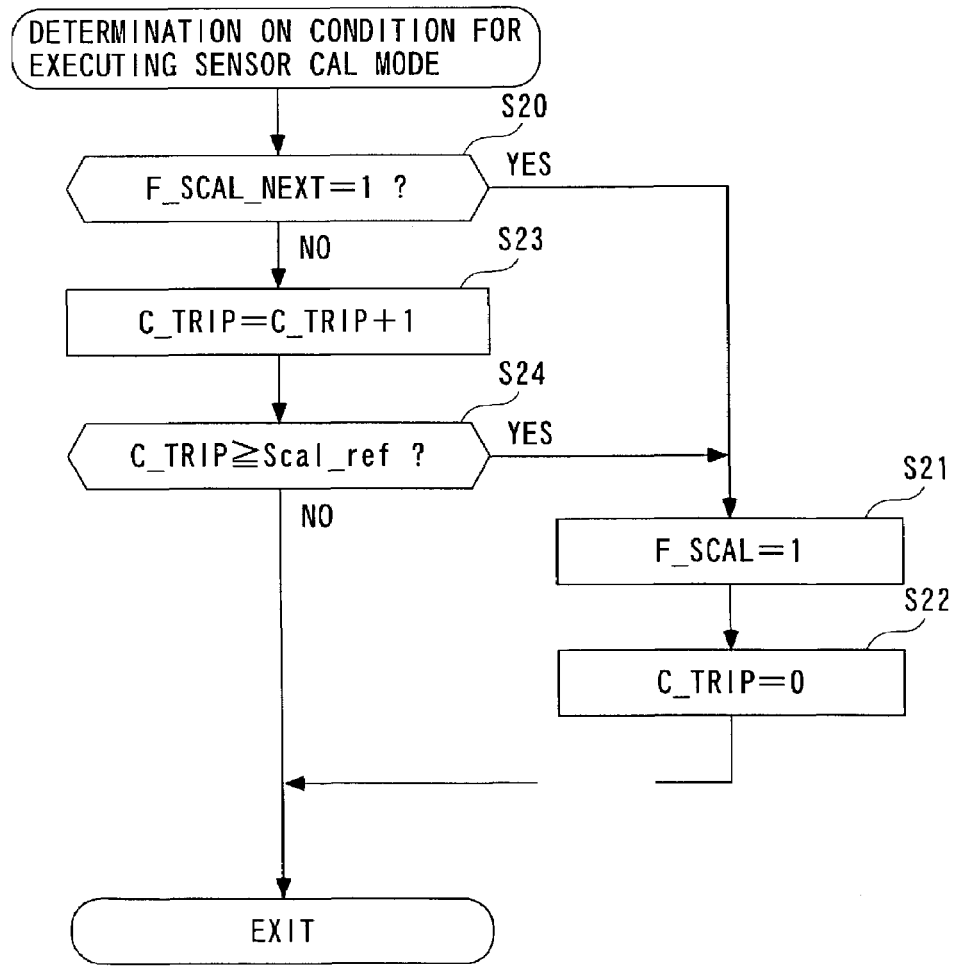
FIG. 5 is a flow chart illustrating a routine for determining a condition for executing a sensor CAL mode.

FIG. 5 illustrates a routine for determining whether or not the condition is established for executing the sensor CAL mode at step 2 in FIG. 3. This routine is executed only once when the engine 2 is started. First, at step 20, it is determined whether or not a sensor CAL mode request flag F_SCAL_NEXT is "1." The CPU sets the sensor CAL mode request flag F_SCAL_NEXT to "1" when a high temperature recovery mode, later described, is executed in the preceding operation.

If the answer to step 20 is YES, showing that the high temperature recovery mode was executed in the preceding operation, the CPU sets the execution condition establishment flag F_SCAL to "1" on the assumption that the condition is established for executing the sensor CAL mode (step 21), and resets an operation counter C_TRIP to zero (step 22), followed by termination of the sensor CAL mode execution determining routine.

On the other hand, if the answer to step 20 is NO, showing that the high temperature recovery mode was not executed in the preceding operation, the CPU increments the operation counter C_TRIP (step 23), and determines whether or not the value indicated by the operation counter C_TRIP is equal to or larger than a predetermined number of times Scal_ref (for example, 30) (step 24). If the answer to step 24 is NO, i.e., when the number of times of operations in which the sensor CAL mode is not executed is below the predetermined number of times Scal_ref, the sensor CAL mode execution determining routine is terminated without further processing.

On the other hand, if the answer to step 24 is YES, i.e., when the sensor CAL mode has not been continuously executed for the predetermined number of operations, the routine proceeds to the aforementioned steps 21, 22, on the assumption that the condition is established for executing the sensor CAL mode, followed by termination of the sensor CAL mode execution determining routine. As described above, the sensor CAL mode is executed when the high temperature recovery mode was executed in the preceding operation, or when the sensor CAL mode has not been continuously executed the predetermined number of times.

Figure 6:
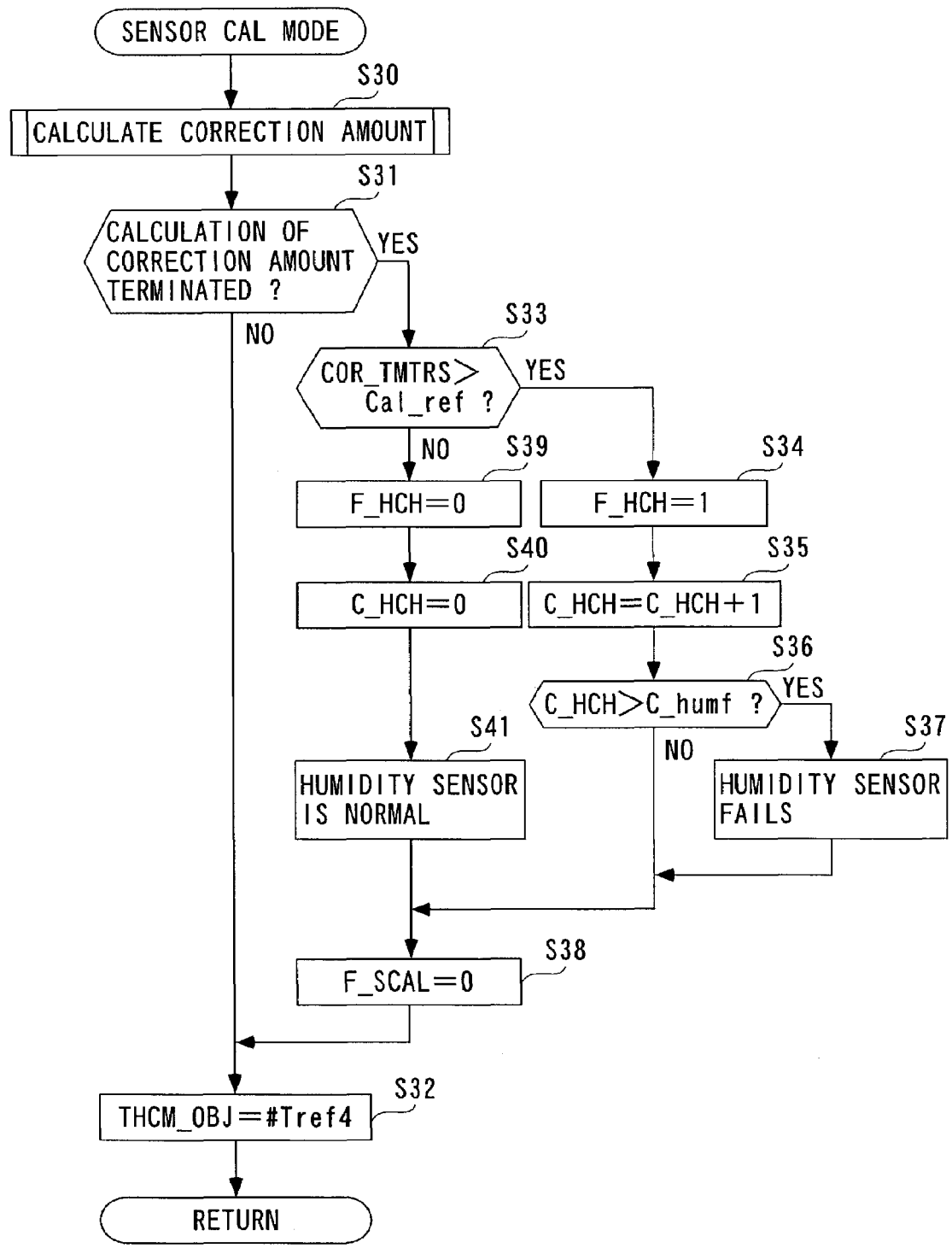
FIG. 6 is a flow chart illustrating a subroutine of the sensor CAL mode at step 2 in FIG. 3.

FIG. 6 illustrates a subroutine of the sensor CAL mode at step 2 in FIG. 3. This subroutine involves a calculation of the correction amount COR_TMTRS indicative of the degree of a change in the characteristic of the humidity sensor 19 based on a result detected thereby, and a determination on a deterioration of the humidity sensor 19 based on the correction value COR_TMTRS. The sensor CAL mode subroutine is executed every predetermined time (for example, 100 ms) in an idle operating condition immediately after the engine 2 starts operating.

Figure 7:
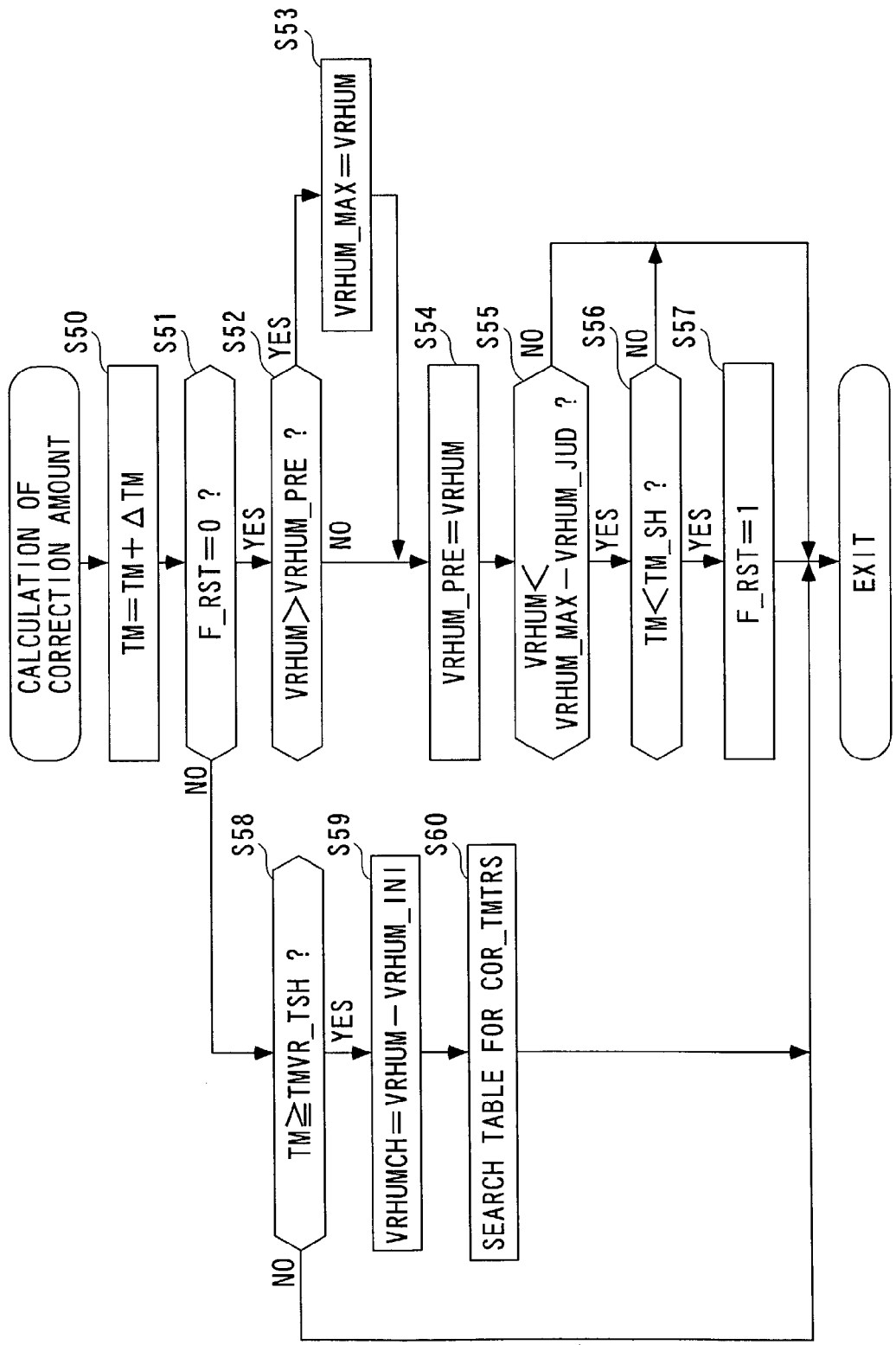
FIG. 7 is a flow chart illustrating a subroutine for calculating a correction amount at step 30 in FIG. 6.

First, at step 30, the CPU calculates the correction amount COR_TMTRS. FIG. 7 illustrates a subroutine for calculating the correction amount COR_TMTRS. The calculation of the correction amount COR_TMTRS is based on the following policy. As a certain time has elapsed from a start of the engine 2, the adsorbent 10 is saturated with moisture adsorbed thereby, causing an increase in the humidity downstream of the adsorbent 10 as well as a monotonous decrease of the detected value VRHUM from the humidity sensor 19. Also, when humidity sensor 19 is deteriorated, the detected value VRHUM begins decreasing at a later timing with a slower slope of the decrease. Thus, the correction amount COR_TMTRS is calculated based on a change in the characteristic of the humidity sensor 19.

In the correction amount calculation subroutine, it is first determined at step 50 whether or not a correction amount calculation enable flag F_RST is "0" after a post-start timer TM is increased by a predetermined value ΔTM (step 51). The post-start timer TM and correction amount calculation enable flag F_RST are reset to "0" at the time the engine 2 is started. Therefore, the answer to step 51 is YES immediately after a start of the engine 2, in which case it is determined whether or not the detected value VRHUM from the humidity sensor 19 is larger than its preceding value VRHUM_PRE (step 52). If the answer to step 52 is YES, indicating that VRHUM>VRHUM_PRE, the CPU sets the detected value VRHUM to a maximum detected value VRHUM_MAX (step 53). Then, the subroutine proceeds to next step 54.

On the other hand, if the answer to step 52 is NO, indicating that VRHUM≦VRHUM_PRE, the subroutine directly proceeds to step 54, where the CPU sets the detected value VRHUM as its preceding value VRHUM_PRE. As is apparent from the foregoing operations, the maximum detected value VRHUM_MAX indicates a maximum of the detected value VRHUM after the start of the engine 2, and corresponds to a minimum relative humidity detected by the humidity sensor 19. Next, it is determined whether or not the detected value VRHUM is smaller than a difference resulting from a subtraction of a predetermined value VRHUM_JUD from the maximum detected value VRHUM_MAX (step 55).

If the answer to step 55 is NO, indicating that VRHUM≧(VRHUM_MAX−VRHUM_JUD), the correction value calculation subroutine is terminated on the assumption that the detected value VRHUM is not stably decreasing. On the other hand, if the answer to step 55 is YES, it is determined whether or not the value indicated by the post-start time TM is smaller than a first predetermined value TM_SH on the assumption that the detected value VRHUM is stably decreasing, i.e., the relative humidity has risen up (step 56). The first predetermined value TM_SH is set in accordance with the resistance value LBLR of the aforementioned label resistive element.

If the answer to step 56 is NO, indicating that TM≧TM_SH, i.e., when a predetermined time corresponding to the first predetermined value TM_SH has elapsed after the engine 2 had started, the correction amount calculation subroutine is terminated without further processing on the assumption that the correction amount COR_TMTRS cannot be properly calculated due to the detected value VRHUM which begins decreasing at a timing too late.

On the other hand, if the answer to step 56 is YES, the CPU sets the correction amount calculation enable flag F_RST to "1" on the assumption that the correction amount COR_TMTRS can be properly calculated (step 57), followed by termination of the correction amount calculation subroutine.

Since the answer to step 51 is NO after step 57 was executed, it is determined whether or not the value indicated by the post-start timer TM is equal to or larger than a second predetermined value TMVR_TSH (step 58). The second predetermined value TMVR_TSH is also set in accordance with the resistance value LBLR of the label resistive element. If the answer to step 58 is NO, showing that TM<TMVR_TSH, the correction amount calculation subroutine is terminated without further processing.

If the answer at step 58 is YES, showing that TM≧TMVR_TSH, i.e., when a predetermined time corresponding to the second predetermined value TMVR_TSH has elapsed after the engine 2 had started, the CPU set a difference resulting from a subtraction of a predetermined value VRHUM_INI from the detection value VRHUM at this time as a parameter RHUMCH (step 59). The predetermined value VRHUM_INI corresponds to a detected value which should be indicated by a new humidity sensor 19 when the predetermined time has elapsed after the start of the engine 2. Thus, the parameter VRHUMCH calculated at step 59 indicates the degree of a change in the characteristic of the humidity sensor 19.

Next, at step 60, the CPU searches a table, not shown, for the correction amount COR_TMTRS based on the parameter VRHUMCH calculated at step 59, followed by termination of the correction amount calculation subroutine. In the table, the correction amount COR_TMTRS is set to a larger value as the parameter VRHUMCH is larger. In other words, the correction amount COR_TMTRS is larger as the characteristic of the humidity sensor 19 changes to a larger degree.

Turning back to FIG. 6, at step 31 subsequent to step 30, it is determined whether or not the calculation of the correction amount at step 30 is terminated. If the answer to step 31 is NO, the CPU sets a target temperature THCM_OBJ of the sensor element temperature THCM to a fourth predetermined temperature #Tref4 (for example, 50° C.) lower than the second predetermined temperature #Tref2 (step 32), followed by termination of the sensor CAL mode subroutine. In this way, the sensor element temperature THCM is controlled to the fourth predetermined temperature #Tref4 by controlling the energization duty ratio DUTY for the heater 21 in a feedback manner with the target temperature THCM_OBJ set to the fourth predetermined temperature #Tref4 at step 6 in FIG. 3 during the calculation of the correction amount COR_TMTRS.

On the other hand, if the answer to step 31 is YES, showing that the correction amount COR_TMTRS has been calculated, it is determined whether or not the calculated correction amount COR_TMTRS is larger than a predetermined reference value Cal_ref (step 33).

If the answer to step 33 is YES, showing that COR_TMTRS>Cal_ref, the CPU sets a high temperature recovery mode execution enable flag F_HCH to "1" to execute the high temperature recovery mode to eliminate a possible deterioration of the humidity sensor 19 due to impurities sticking on the sensor element 19a or the like, as can be determined from a large change in the characteristic of the humidity sensor 19 (step 34). Then, the CPU increments a counter C_HCH which counts the number of times the high temperature recovery mode is executed (step 35). The high temperature recovery mode is intended to recover a detection accuracy of the humidity sensor 19 by heating the sensor element 19a to an extremely high temperature using the heater 21 to remove impurities sticking on the sensor element 19a. Details on the high temperature recovery mode will be described later. Next, it is determined whether or not the value indicated by the counter C_HCH is larger than a predetermined value C_humf (for example, 3) (step 36).

IF the answer to step 36 is NO, showing that the high temperature recovery mode has been executed equal to or less than the predetermined number of times, the CPU resets the execution condition establishment flag F_SCAL to "0" on the assumption that the detection accuracy of the humidity sensor 19 can be recovered by executing the high temperature recovery mode. Then, the CPU executes the aforementioned step 32, followed by termination of the sensor CAL mode subroutine.

If the answer to step 36 is YES, showing that the correction amount COR_TMTRS cannot be reduced to the reference value Cal_ref or less even though the high temperature recovery mode is continuously executed the predetermined number of time, the CPU determines that the humidity sensor 19 fails from the fact that the humidity sensor 19 presents a large change in the characteristic and therefore cannot be recovered to a normal condition (step 37). Then, the subroutine proceeds to step 38 onward. In response, the alarm lamp 23 is turned on to indicate the failure of the humidity sensor 19.

On the other hand, if the answer to step 33 is NO, showing that COR_TMTRS≦Cal_ref, the CPU sets the high temperature recovery mode execution enable flag F_HCH to "0" on the assumption that the humidity sensor 19 presents a small change in the characteristic so that the high temperature recovery mode need not be executed (step 39), resets the counter C_HCH to "0" (step 40), and determines that the humidity sensor 19 is normal (step 41). Subsequently, the CPU executes the aforementioned steps 38 and 32, followed by termination of the sensor CAL mode subroutine.

Figure 8:
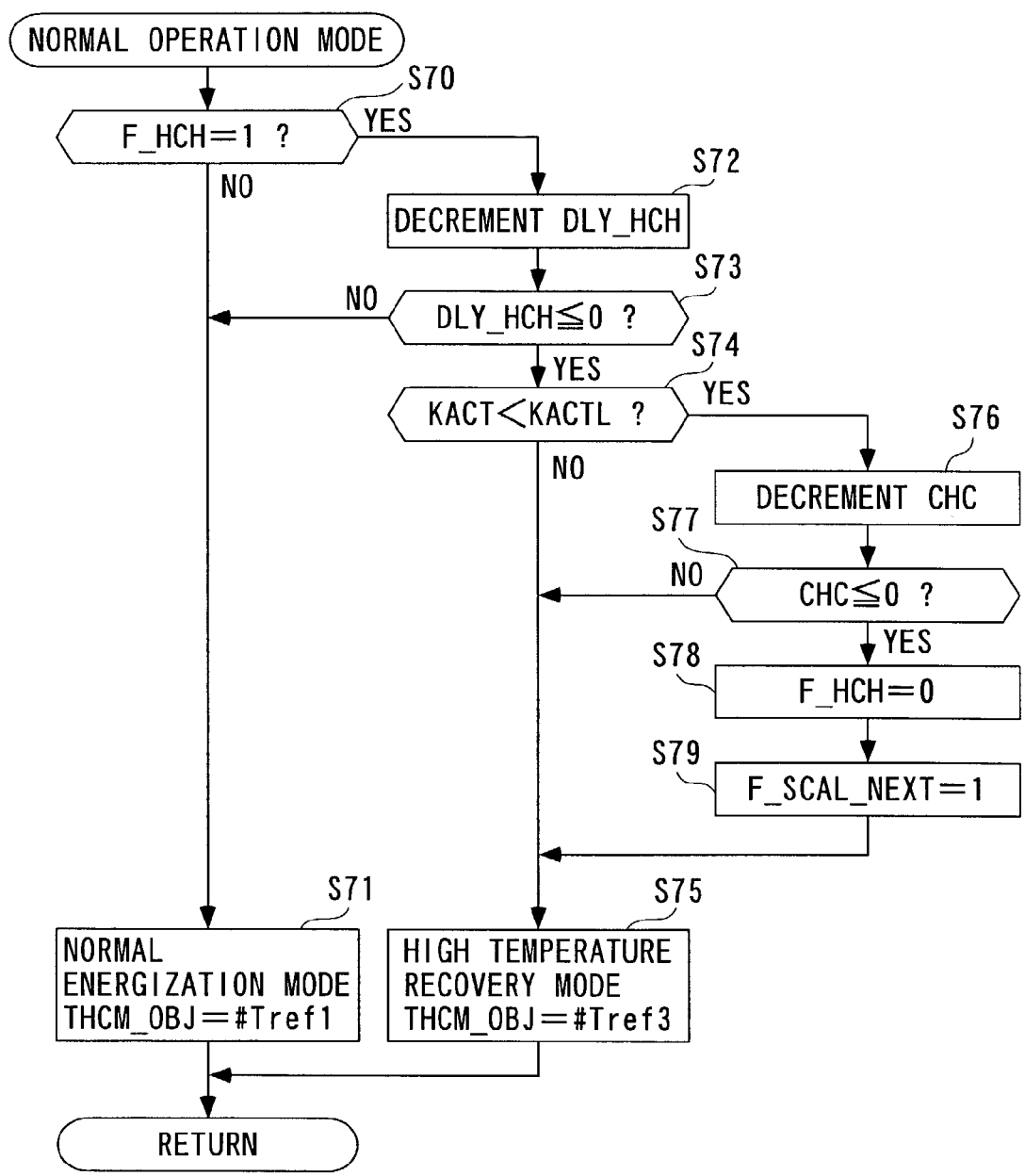
FIG. 8 is a flow chart illustrating a subroutine of a normal operation mode at step 5 in FIG. 3.

FIG. 8 illustrates a subroutine of the normal operation mode executed at step 5 in FIG. 3. First, at step 70, it is determined whether or not the high temperature recovery mode execution enable flag F_HCH is "1." If the answer to step 70 is NO, showing that the high temperature recovery mode is not enabled, the CPU sets the target temperature THCM_OBJ to a first predetermined temperature #Tref1 (for example, 600° C.) higher than the second predetermined temperature #Tref2 to execute a normal energization mode (step 71), followed by termination of the normal operation mode subroutine.

On the other hand, if the answer to step 70 is YES, showing that the high temperature recovery mode is enabled, the CPU decrements a delay timer DLY_HCH (step 72), and determines whether or not the value indicated by the delay timer DLY_HCH is equal to or less than zero (step 73). The delay timer DLY_HCH is set to a predetermined value (for example, corresponding to 300 seconds) at the time the normal operation mode is started.

If the answer to step 73 is NO, showing that a predetermined time has not elapsed from the start of the normal operation mode, the CPU executes step 71 to continue the normal energization mode, followed by termination of the normal operation mode subroutine.

If the answer to step 73 is YES, showing that the predetermined time has elapsed from the start of the normal operation mode, the CPU executes the high temperature recovery mode at step 75 irrespective of the result of determination at step 74. Then, it is determined whether or not the value KACT detected by the LAF sensor 22 is smaller than a predetermined value KACTL (for example, 0.95) (step 74).

If the answer to step 74 is NO, showing that the humidity sensor 19 is not in a lean atmosphere, the subroutine immediately proceeds to step 75, where the CPU sets the target temperature THCM_OBJ to a third predetermined temperature #Tref3 (for example, 900° C.) higher than the first predetermined temperature #Tref1 to execute the high temperature recovery mode (step 75), followed by termination of the normal operation mode subroutine. In the foregoing manner, the delay time provided at a transition from the normal energization mode to the high temperature recovery mode permits a transition to the high temperature recovery mode after the sensor element temperature THCM is increased without fail in the normal energization mode, thereby reducing a burden on the sensor element 19a.

If the answer to step 74 is YES, showing that the humidity sensor 19 is in a lean atmosphere, the CPU decrements the counter CHC (step 76), and determines whether or not the value indicated by the counter CHC is equal to or less than zero (step 77). The counter CHC is set to a predetermined value (for example, corresponding to 60 seconds) at the time the normal operation mode is started.

If the answer to step 77 is NO, the CPU executes step 75 to continue the high temperature recovery mode, followed by termination of the normal operation mode subroutine.

On the other hand, if the answer to step 77 is YES, i.e., when the high temperature recovery mode has been executed for a predetermined time with the humidity sensor 19 remaining in the lean atmosphere, the CPU resets the high temperature recovery mode execution enable flag F_HCH to "0" to terminate the high temperature recovery mode on the assumption that the high temperature recovery mode has been sufficiently executed in an oxidizing condition (step 78). After setting the sensor CAL mode request flag F_SCAL_NEXT to "1" (step 79), the CPU executes the aforementioned step 75, followed by termination of the normal operation mode subroutine. The execution of step 78 causes the answer at step 70 to be NO in the next loop, causing a transition from the high temperature recovery mode to the normal supply node. Also, the execution of step 79 causes the answer at step 20 in FIG. 5 to be YES in the next operation, so that the sensor CAL mode is executed.

Figure 9:
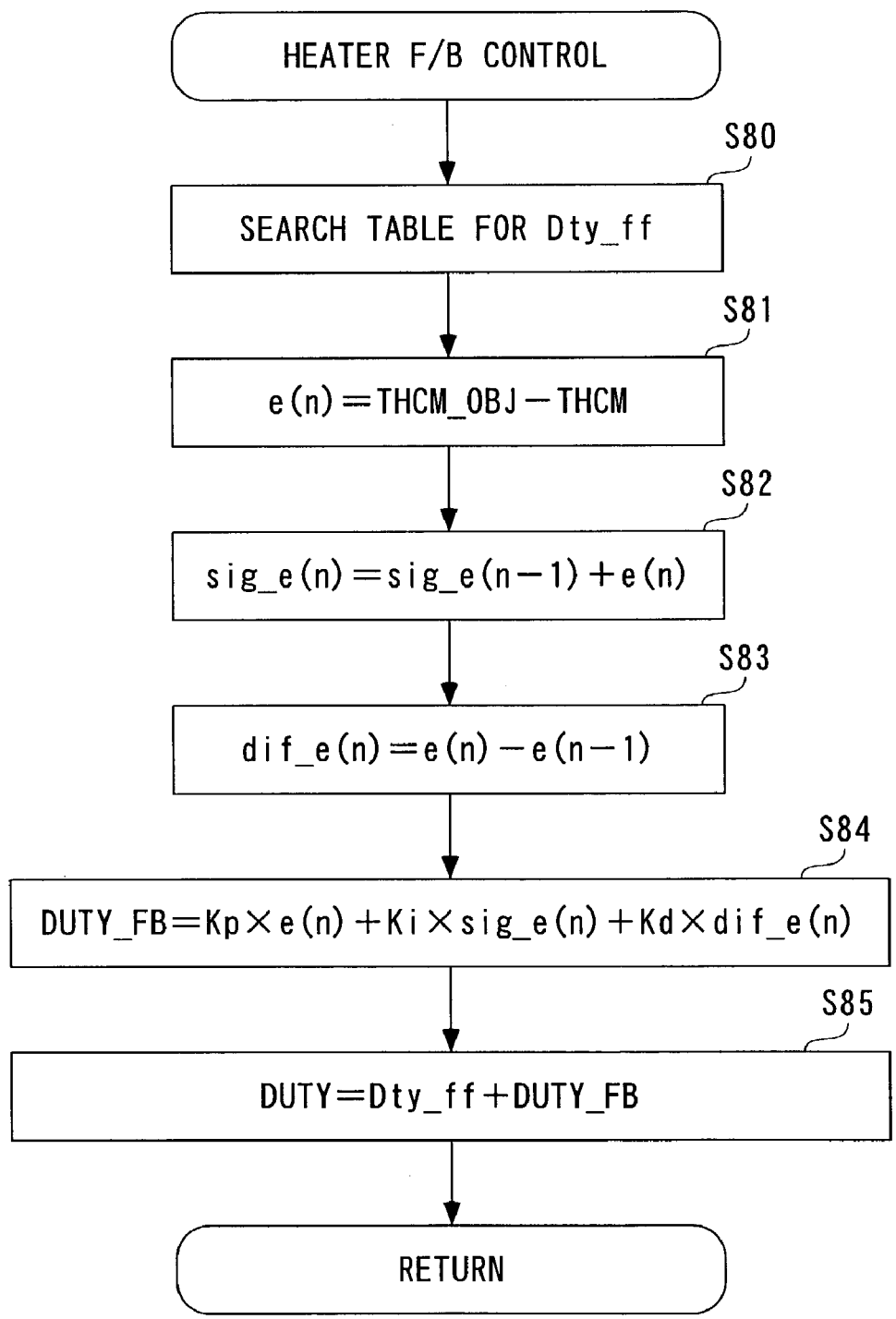
FIG. 9 is a flow chart illustrating a subroutine of a heater F/B control at step 6 in FIG. 3.

FIG. 9 illustrates a subroutine of the hater F/B control executed at step 6 in FIG. 3. First at step 80, the CPU searches a table, not shown, for a reference value Dty_ff for the energization duty ratio DUTY in accordance with the target temperature THCM_OBJ. In this table, the reference value Dyt_ff is set to a larger value as the target temperature THCM_OBJ is higher.

Next, at step 81, the CPU calculates a deviation e(n) of the sensor element temperature THCM from the target temperature THCM_OBJ. Next, the CPU adds the current deviation e(n) to its preceding value sig_e (n−1) to calculate an integrated value sig_e (n) of the deviation e(n) (step 82), and subtracts the preceding value e (n−1) from the current deviation e (n) to calculate a changing amount dif_e(n) of the deviation (step 83).

Next, the CPU calculates an F/B control term DUTY_FB of the energization duty ratio DUTY in accordance with the following equation (step 84):

$$DUTY\_FB = Kp \times e(n) + Ki \times sig\_e(n) + Kd \times dif\_e(n)$$

where Kp, Ki, and Kd are a P-term gain, an I-term gain, and a D-term gain, respectively.

Then, the CPU adds the F/B control term DUTY_FB to the reference value Dty_ff retrieved at step 80, and sets the resulting sum to the energization duty ratio DUTY (step 85), followed by termination of the heater F/B control subroutine.

Figure 10:
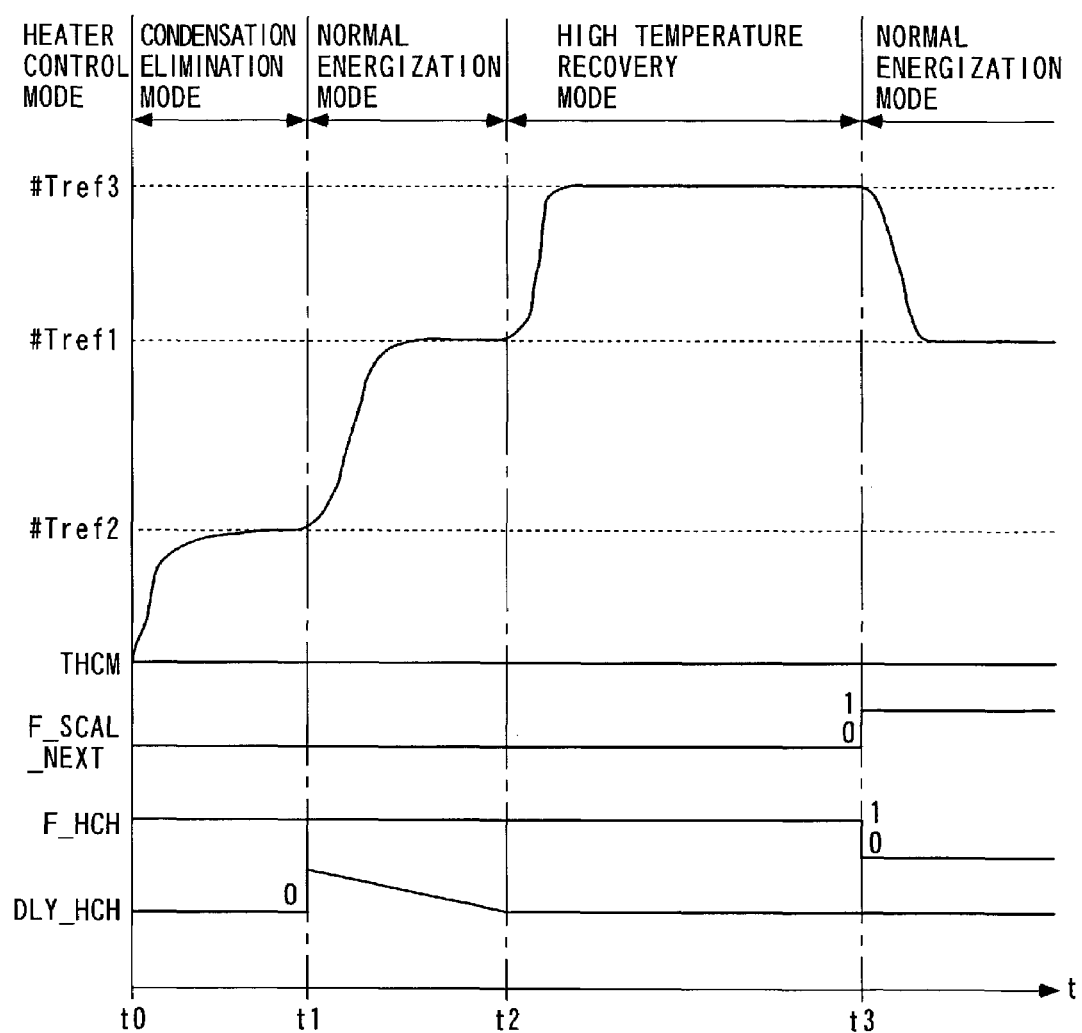
FIG. 10 is a timing chart showing an exemplary operation which is performed when a high temperature recovery mode is enabled and the condition is not met for executing the sensor CAL mode.
Figure 11:
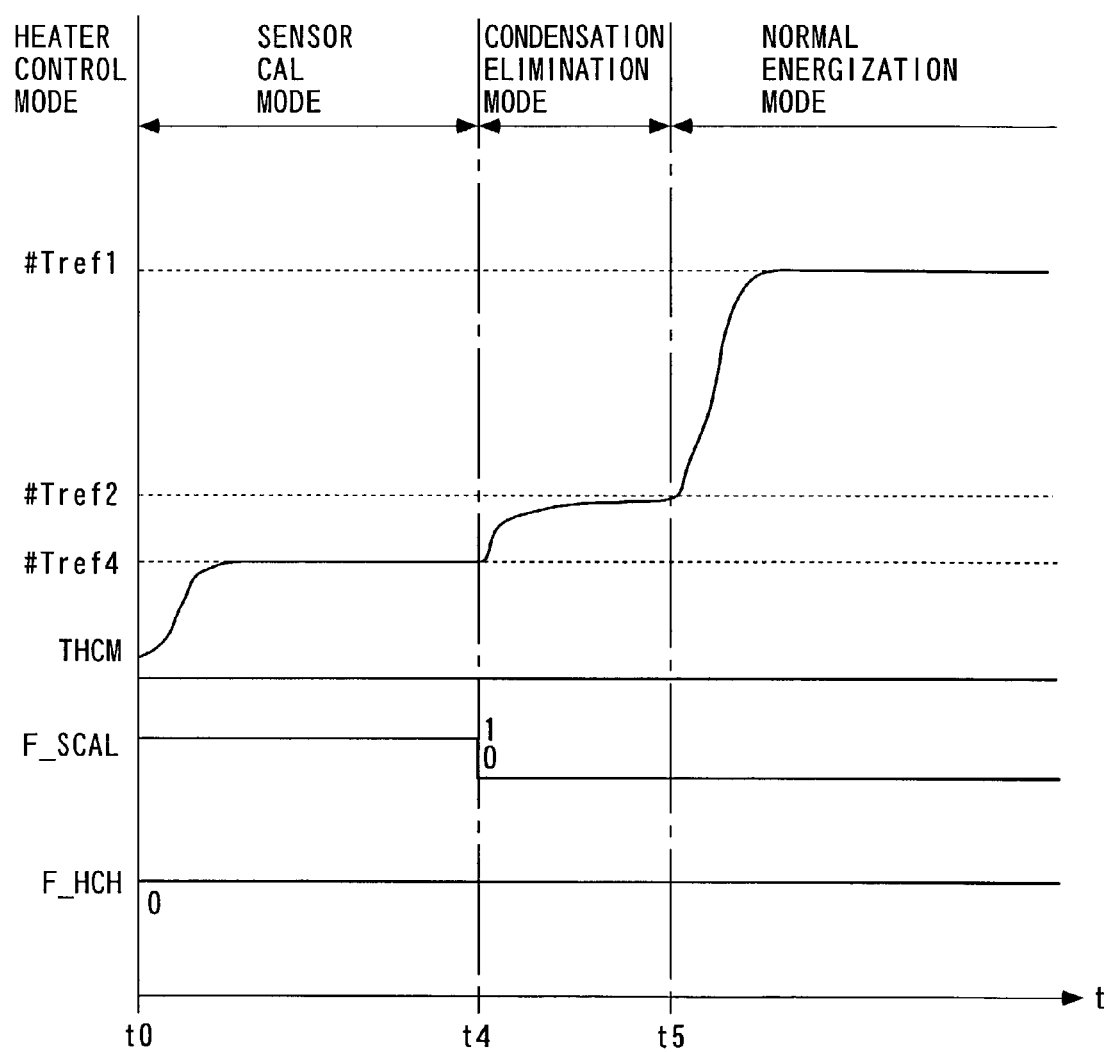
FIG. 11 is a timing chart showing an exemplary operation which is performed when the condition is not met for executing the sensor CAL mode.

FIGS. 10 and 11 show two exemplary operations resulting from the so far described heater control procedure. FIG. 10 shows the operation when the high temperature recovery mode is enabled (F_HCH=1) during the preceding operation and the condition is not established for executing the sensor CAL mode (F_SCAL=0) at the start of the engine 2. As shown in FIG. 10, when the sensor element temperature THCM is equal to or lower than the second predetermined temperature #Tref2 upon start of the engine 2 (at time t0), the CPU sets the heater control mode to the condensation elimination mode (at step 4 in FIG. 3), and sets the energization duty ratio DUTY for the heater 21 to the small predetermined value Dty_st. Then, when the sensor element temperature THCM exceeds the second predetermined temperature #Tref2 (at time t1), the CPU switches the heater control mode to the normal energization mode within the normal operation mode (at step 5 in FIG. 3), and sets the delay timer DLY_HCH. In the normal energization mode, the CPU controls the energization duty ratio DUTY in a feedback manner with the target temperature THCM_OBJ set to the first predetermined temperature #Tref1, thereby controlling the sensor element temperature THCM to the first predetermined temperature #Tref1.

As a predetermined time has elapsed after the transition to the normal energization mode (at time t2), the value indicated by the delay timer DLY_HCH reaches zero, causing the CPU to switch the heater control mode to the high temperature recovery mode. In the high temperature recovery mode, the CPU controls the energization duty ratio DUTY in a feedback manner with the target temperature THCM_OBJ set to the third predetermined temperature Tref3 higher than in the normal energization mode, thereby controlling the sensor element temperature THCM to the third predetermined temperature #Tref3. Then, when the high temperature recovery mode has been executed for a predetermined time with the humidity sensor 19 remaining in the lean atmosphere (at time t3), the CPU again switches the heater control mode to the normal energization mode. Also, upon switching, the CPU resets the high temperature recovery mode execution enable flag F_HCH to "0" and sets the sensor CAL mode request flag F_SCAL_NEXT to "1."

FIG. 11 is an exemplary operation when the condition is established for executing the sensor CAL mode. In this event, the CPU sets the heater control mode to the sensor CAL mode after the engine 2 is started (at step 2 in FIG. 3). In the sensor CAL mode, the CPU controls the energization duty ratio DUTY in a feedback manner with the target temperature THCM_OBJ set to the lowest fourth predetermined temperature #Tref4, thereby controlling the sensor element temperature THCM to the fourth predetermined temperature #Tref4. Then, the CPU calculates the correction amount COR_TMTRS. At the end of the sensor CAL mode (at time t4), the CPU resets the execution condition establishment flag F_SCAL to "0" and sets the high temperature recovery mode execution enable flag F_HCH to "1" or "0" depending on the calculated correction amount COR_T-MTRS. This example takes the latter value.

When the sensor element temperature THCM is equal to or lower than the second predetermined temperature #Tref2 at the end of the sensor CAL mode, the CPU switches the heater control mode to the condensation elimination mode. Subsequently, when the sensor element temperature THCM exceeds the second predetermined temperature #Tref2 (at time t5), the CPU switches the heater control mode to the normal energization mode. In this example, since the high temperature recovery mode execution enable flag F_HCH is set to "0," the CPU does not execute the high temperature recovery mode but continuously executes only the normal energization mode, unlike the example shown in FIG. 10.

As described above, according to the foregoing embodiment, the CPU controls the sensor element temperature THCM in a feedback manner to the first predetermined temperature #Tref1 during an operation of the engine 2. It is therefore possible to prevent impurities in exhaust gases from sticking on the sensor element 19a by maintaining the sensor element 19 at a high temperature while minimizing the power consumed by the heater 21 during the operation of the engine 2. Consequently, the detection accuracy of the humidity sensor 19 can be maintained high.

On the other hand, when the sensor element temperature THCM is lower than the second predetermined temperature #Tref2 so that condensation can occur, the CPU executes the condensation elimination mode to control the heater 21 with the energization duty ratio DUTY smaller than that in the normal operation mode. As a result, the sensor element temperature THCM slowly rises, thereby making it possible to eliminate the condensation with minimum power consumption while ensuring the prevention of the sensor element 19a from cracking due to a sudden change in temperature.

Further, the CPU controls the sensor element temperature THCM in a feedback manner to the lowest fourth predetermined temperature #Tref4 in the sensor CAL mode, permitting the humidity sensor 19 to present a detection result with the sensor element 19a converged to a temperature at which the sensor element 19a exactly presents a change in the characteristic thereof. As such, the correction amount COR_TMTRS can be properly calculated based on the detection result.

In addition, when a large correction amount COR_TMTRS is required, i.e., when the humidity sensor 19 largely changes in the characteristic, the CPU executes the high temperature recovery mode to control the sensor element temperature THCM in a feedback manner to the highest third predetermined temperature #Tref3. Therefore, when the large correction amount COR_TMTRS is required due to impurities in exhaust gases sticking on the sensor element 19a, the impurities can be removed at a high temperature, while minimizing the power consumption of the heater 21, thereby recovering the original characteristic of the humidity sensor 19 and hence the detection accuracy of the same.

It should be understood that the present invention is not limited to the embodiment described above, but may be practiced in a variety of manners. For example, the values of the first to fourth predetermined temperatures #tref1–#tref4 shown in the embodiment are illustrative in any sense, and different values may be used therefor as long as they achieve the respective purposes. Particularly, as the first predetermined temperature #Tref1 is set higher, impurities are further prevented from sticking on the sensor element 19a, whereas the heater 21 consumes larger power, so that an appropriate value should be found therefor, for example, from a range of 300 to 800° C. through experiments and the like to well balance both requirements. On the other hand, since the third predetermined temperature #Tref3 is intended to remove impurities which stick on the sensor element 19a even if the sensor element temperature THCM is maintained at the first predetermined temperature #Tref1, an appropriate value higher than the first predetermined temperature #Tref1 should be found, for example, from a range of 600 to 1000° C. in a similar manner.

Figure 12:
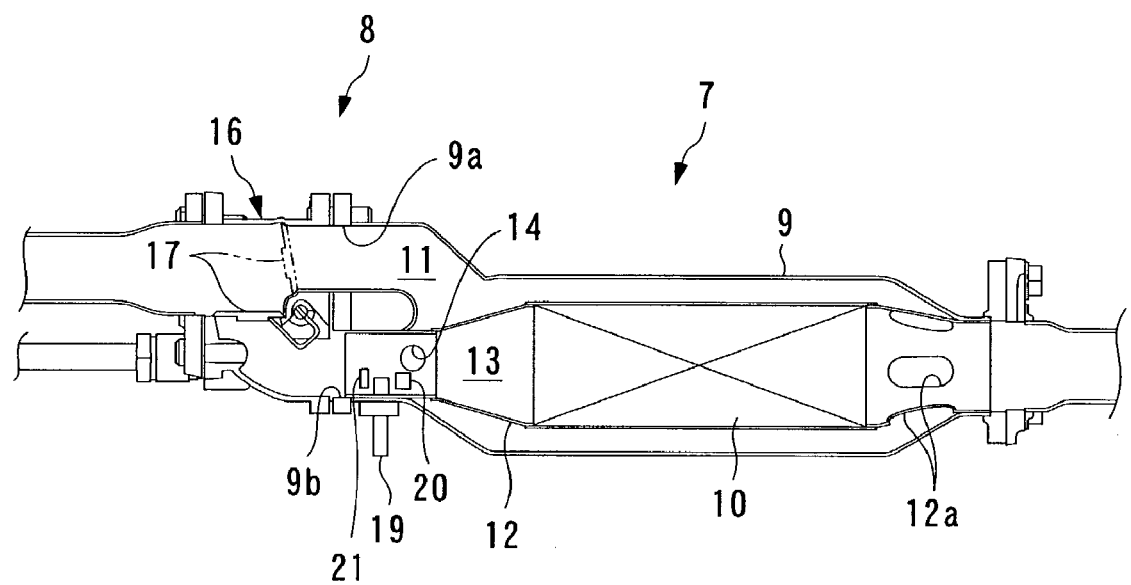
FIG. 12 is an enlarged cross-sectional view illustrating a hydrocarbon adsorber which has a humidity sensor disposed at a location upstream of an adsorbent.

Likewise, the hydrocarbon adsorber 7 including the humidity sensor 19, shown in FIG. 2, is also illustrative, and it goes without saying that the present invention may be applied to any humidity sensor contained in a hydrocarbon adsorber 7 in a different configuration. FIG. 12 illustrates an example of a different hydrocarbon adsorber which comprises a humidity sensor 19 disposed at a location upstream of an adsorbent 10; and a temperature sensor 20 and a heater 21 disposed near the humidity sensor 19. The adsorbent 10 is determined in regard to a deterioration based on a humidity detected by the humidity sensor 19 when a switching valve 17 closes a bypass exhaust passage 13 after the operation of an engine 2 is stopped. Specifically, the adsorbent 10 is determined in regard to a deterioration based on the humidity detected by the humidity sensor 19 at that time, from the fact that the humidity becomes lower in a closed space between the switching valve 17 and the adsorbent 10 as the adsorbent 10 is cooled down to recover its adsorbing ability after the operation of the engine 2 is stopped. The present invention can be similarly applied to a temperature control for the humidity sensor 19 as described above.

As will be appreciated from the foregoing, the temperature control apparatus for a humidity sensor according to the present invention can advantageously prevent impurities from sticking on the sensor element without causing cracking of the sensor element even if it is heated by the heater when condensation occurs, thereby maintaining a high detection accuracy of the humidity sensor.

What is claimed is:

1. A temperature control apparatus for controlling a temperature of a sensor element of a humidity sensor disposed in an exhaust passage of an internal combustion engine for detecting a humidity within said exhaust passage, in order to determine deterioration of an adsorbent for adsorbing hydrocarbons in an exhaust gas, said apparatus comprising:
   a heater for heating said sensor element;
   temperature detecting means for detecting the temperature of said sensor element; and
   heater control means for continuously controlling the heater during an operation of said internal combustion engine to converge the detected temperature to a first predetermined temperature, in the range of 300 to 800 degrees Celsius, for avoiding impurities in the exhaust gas from sticking on said sensor element.

2. A temperature control apparatus for a humidity sensor according to claim 1, wherein said heater is configured to vary its heating amount in response to the amount of power supplied thereto, wherein said heater control means controls said amount of power supplied to said heater in a feedback manner to bring the temperature of said sensor element to said first predetermined temperature.

3. A temperature control apparatus for a humidity sensor according to claim 1, wherein said heater control means controls said heater with a smaller heating amount when the temperature of said sensor element is lower than a second predetermined temperature lower than said first predetermined temperature.

4. A temperature control apparatus for a humidity sensor according to claim 3, further comprising:
characteristic change parameter calculating means for calculating a characteristic change parameter indicative of a degree of a change in the characteristic of said humidity sensor based on a result detected by said humidity sensor,
wherein said heater control means further controls said sensor element to a third predetermined temperature or higher, said third temperature being higher than said first predetermined temperature, when the calculated characteristic change parameter is larger than a predetermined value.

5. A temperature control apparatus for a humidity sensor according to claim 4, wherein said heater control means further controls said sensor element to a fourth predetermined temperature or lower, said fourth predetermined temperature being lower than said second predetermined temperature, while said characteristic change parameter calculating means is calculating said characteristic change parameter.

* * * * *